United States Patent
Lin et al.

(10) Patent No.: US 10,912,936 B2
(45) Date of Patent: Feb. 9, 2021

(54) TUBE-DOCKING HOLDING DEVICE

(71) Applicants: National Formosa University, Yunlin County (TW); National Taiwan University Hospital Yun-Lin Branch, Douliu (TW)

(72) Inventors: Sung-An Lin, Chu-Nan Township (TW); I-En Lin, Yunlin County (TW); Feng-Jung Yang, Douliu (TW); Hao-Ting Chiang, Yunlin County (TW)

(73) Assignees: National Formosa University, Yunlin County (TW); National Taiwan University Hospital Yun-Lin Branch, Douliu (TW)

( * ) Notice: Subject to any disclaimer, the term of this patent is extended or adjusted under 35 U.S.C. 154(b) by 113 days.

(21) Appl. No.: 16/148,701

(22) Filed: Oct. 1, 2018

(65) Prior Publication Data
US 2020/0101276 A1 Apr. 2, 2020

(51) Int. Cl.
*A61M 39/18* (2006.01)
*A61M 1/28* (2006.01)
*A61M 39/10* (2006.01)
*A61M 39/20* (2006.01)

(52) U.S. Cl.
CPC ............ *A61M 39/18* (2013.01); *A61M 1/285* (2013.01); *A61M 39/1011* (2013.01); *A61M 39/20* (2013.01)

(58) Field of Classification Search
CPC .................. A61M 1/285; A61M 39/20; A61M 2039/1027; A61M 2039/1033; A61M 2039/1066; A61M 39/1011; A61M 39/12; A61M 39/18; A61M 39/10; A61M 25/001
See application file for complete search history.

(56) References Cited

U.S. PATENT DOCUMENTS

| | | | | |
|---|---|---|---|---|
| 5,286,067 A * | 2/1994 | Choksi | ................. | A61M 39/10 285/331 |
| 2014/0100548 A1* | 4/2014 | Lyons | ................. | A61M 39/162 604/508 |
| 2014/0207118 A1* | 7/2014 | Tsoukalis | ............. | A61M 39/20 604/535 |

* cited by examiner

*Primary Examiner* — Lauren P Farrar
*Assistant Examiner* — Hamza A Darb (57) ABSTRACT

A tube-docking holding device includes a first connector bracket and a second connector bracket. The first connector bracket includes two shells. When the two shells are closed, a first accommodation space is surrounded for fixing a portion of a first connector assembly of a catheter. The second connector bracket includes a base body and a cover body. The base body includes a first inner shell and a first outer shell. The cover body includes a second inner shell and a second outer shell. When the cover body and the base body are closed, the first inner shell and the second inner shell surround and define a second accommodation space for fixing a portion of a second connector assembly of a dialysate tube. An interconnected guiding space is formed between the first inner shell and the first outer shell and between the second inner shell and the second outer shell.

8 Claims, 7 Drawing Sheets

TUBE-DOCKING HOLDING DEVICE

FIELD OF THE INVENTION

The present invention relates to a tube-docking holding device, and more particularly to a tube-docking holding device for docking a catheter with a dialysate tube for peritoneal dialysis.

BACKGROUND OF THE INVENTION

Peritoneal dialysis (PD) is an alternative to routine renal hemodialysis and can be performed at home by a patient. The patient to perform peritoneal dialysis needs to place a catheter into the body by surgery. One end portion of the catheter is located outside the patient's body, and peritoneal dialysis can be performed by docking the catheter with a dialysate tube of a dialysis solution exchange bag.

When performing peritoneal dialysis, the patient must follow strict hygiene rules to avoid infection. For example, when the catheter is docked with the dialysate tube, the docking site must be prevented from being touched, and dust and bacteria in the air must be prevented from entering the body to cause infection and to lead to complications such as peritonitis. However, such an action of docking the catheter with the dialysate tube and not easily touching the docking site may be a challenge for patients with physical limitations such as vision loss or hand tremors.

SUMMARY OF THE INVENTION

The present invention provides a tube-docking holding device for assisting in docking and disconnection of a catheter and a dialysate tube for peritoneal dialysis, and for reducing the possibility of contamination in docking and disconnection.

The tube-docking holding device provided by the present invention is adapted for docking a catheter with a dialysate tube for peritoneal dialysis. One end of the catheter is placed into a patient's body. The other end of the catheter is located outside the patient's body and is connectedly provided with a first connector assembly. One end of the dialysate tube is connected to a double-bag system. The other end of the dialysate tube is connectedly provided with a second connector assembly. The tube-docking holding device includes a first connector bracket and a second connector bracket. The first connector bracket includes a lower shell and an upper shell, and the upper shell is opened or closed relative to the lower shell. When the upper shell and the lower shell are closed, a first accommodation space is surrounded and defined for fixing one of a portion of the first connector assembly and a portion of the second connector assembly. The second connector bracket includes a base body and a cover body. The cover body is opened or closed relative to the base body. The base body includes a first inner shell and a first outer shell. A first guiding space is formed between the first inner shell and the first outer shell. The cover body includes a second inner shell and a second outer shell. A second guiding space is formed between the second inner shell and the second outer shell. When the cover body and the base body are closed, the first inner shell and the second inner shell surround and define a second accommodation space for fixing the other one of a portion of the first connector assembly and a portion of the second connector assembly. The first guiding space and the second guiding space are interconnected for insertion and docking of the lower shell and the upper shell which are closed.

In an embodiment of the present invention, the first accommodation space has a first opening end and a second opening end opposite to each other. The lower shell and the upper shell are respectively provided with a fixing portion at an end adjacent to the second opening end. The first connector assembly includes a first connector body. The first connector body has a first end portion. The fixing portions of the lower shell and the upper shell can be used for clamping a portion of the first connector body, so that a portion of the first connector body and the first end portion are located in the first accommodation space. The first end portion is toward the first opening end. The catheter is exposed outside the second opening end.

In an embodiment of the present invention, the tube-docking holding device further includes a cap bushing, an interior of which is provided with two clamped holding portions. The cap bushing can be sleeved on the first connector bracket, so as to cover the first opening end. The first connector assembly further includes a cap. The cap is screwed to the first connector body and covers the first end portion. The two clamped holding portions of the cap bushing can be used for being placed into the first accommodation space and clampedly holding the cap, and the cap and the first connector body are separated through actuation of the cap bushing.

In an embodiment of the present invention, two clamped holding portions of the cap bushing can be used for clamping a cap. The cap bushing is sleeved on the first connector bracket to cover the first opening end, and the two clamped holding portions are placed into the first accommodation space. The cap clamped by the two clamped holding portions is screwed to the first connector body through actuation of the cap bushing.

In an embodiment of the present invention, an inner side surface of at least one of the fixing portions forms a foolproof groove.

In an embodiment of the present invention, the lower shell and the upper shell are arc-shaped shells, and the lower shell and the upper shell, after being closed, form a hollow cylindrical shape.

In an embodiment of the present invention, a side of the upper shell is pivotally connected to the lower shell. A side edge of an outer surface of the lower shell is provided with a first slot. A side edge of the upper shell is extendedly provided with a first fastening portion. When the lower shell and the upper shell are closed, the first fastening portion is fastened to the first slot.

In an embodiment of the present invention, the first inner shell, the second inner shell, the first outer shell and the second outer shell are arc-shaped shells. The first inner shell and the second inner shell, after being closed, constitute an inner ring shell. The first outer shell and the second outer shell, after being closed, constitute an outer ring shell. The inner ring shell and the outer ring shell have the same central axis, and a diameter of the inner ring shell is smaller than a diameter of the outer ring shell.

In an embodiment of the present invention, the second accommodation space has a third opening end and a fourth opening end opposite to each other. An inner surface of at least one of the first inner shell and the second inner shell is provided with a fixing groove. The second connector assembly comprises a second connector body. The second connector body has a second end portion. The fixing groove can be used for fixing a portion of the second connector body, so that the second end portion is located in the second accommodation space. The second end portion is toward the third opening end, and the dialysate tube is exposed outside the fourth opening end.

In an embodiment of the present invention, a side of the cover body is pivotally connected to the base body. A side edge of an outer surface of the base body is provided with a second slot. A side edge of the cover body is extendedly provided with a second fastening portion. When the base body and the cover body are closed, the second fastening portion is fastened to the second slot.

The present invention adopts the first connector bracket and the second connector bracket, which can be opened or closed, for fixing the first connector assembly of the catheter and the second connector assembly of the dialysate tube. The first connector bracket and the second connector bracket can be axially docked to each other, so that when the first connector assembly of the catheter is docked with the second connector assembly of the dialysate tube, the sterile end portions thereof are covered by the tube-docking holding device and physically isolated, thereby preventing the end portions from coining into contact with dust or other contaminants, and helping reduce the possibility of contamination of the catheter and the dialysate tube when connected or disconnected.

BRIEF DESCRIPTION OF THE DRAWINGS

The present invention will become more readily apparent to those ordinarily skilled in the art after reviewing the following detailed description and accompanying drawings, in which.

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
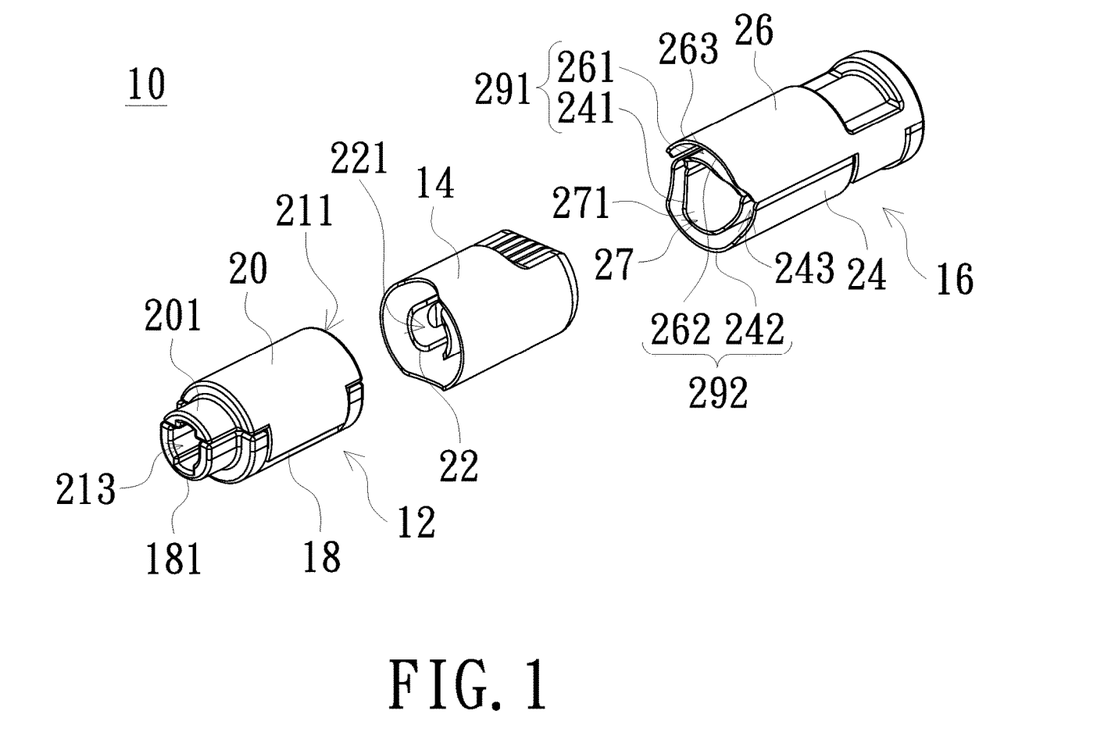
FIG. 1 is a schematic exploded view of a tube-docking holding device according to an embodiment of the present invention.

FIG. 1 is a schematic exploded view of a tube-docking holding device according to an embodiment of the present invention. A tube-docking holding device 10 includes a first connector bracket 12, a cap bushing 14 and a second connector bracket 16. The first connector bracket 12 includes a lower shell 18 and an upper shell 20. A side edge of the upper shell 20 is pivotally connected to a side edge of the lower shell 18, and the upper shell 20 can be opened and closed relative to the lower shell 18. When the upper shell 20 and the lower shell 18 are closed, a first accommodation space 21 (marked in FIG. 3 described below) can be surrounded and defined. The first accommodation space 21 has a first opening end 211 and a second opening end (not numbered) opposite to each other. In one embodiment, the lower shell 18 and the upper shell 20 are arc-shaped shells. The lower shell 18 and the upper shell 20, after being closed, form a hollow cylindrical shape. Ends of the lower shell 18 and the upper shell 20 adjacent to the second opening end are provided with fixing portions 181 and 201, respectively. In one embodiment, each of the two fixing portions 181, 201 is in the shape of a semi-arc. With the closure of the lower shell 18 and the upper shell 20, the two fixing portions 181, 201 are also closed to surround a clamping space 213. The clamping space 213 is interconnected to the second opening end, and an inner diameter of the clamping space 213 is smaller than an inner diameter of the first accommodation space 21.

Figure 2:
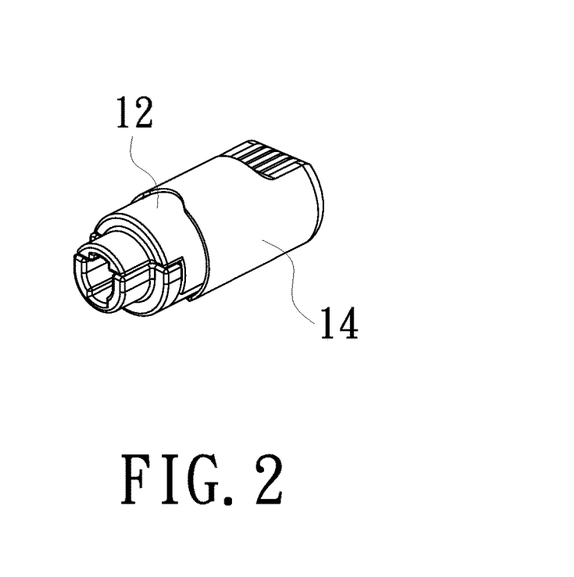
FIG. 2 is a schematic view of a cap bushing sleeved on a first connector bracket of a tube-docking holding device according to an embodiment of the present invention.

As shown in FIG. 1, the internal shape of the cap bushing 14 corresponds to the contour of the first connector bracket 12. The interior of the cap bushing 14 is provided with two clamped holding portions 22. The two clamped holding portions 22 are slightly arc-shaped and form together a clamped holding space 221. As shown in FIG. 2, the cap bushing 14 can be sleeved at the first opening end 211 of the first connector bracket 12, so as to cover the first opening end 211 (shown in FIG. 1) and to place the two clamped holding portions 22 (shown in FIG. 1) into the first accommodation space 21 (shown in FIG. 3). Further, the cap bushing 14 sleeved on the first connector bracket 12 can rotate relative to the first connector bracket 12.

As shown in FIG. 1, the second connector bracket 16 includes a base body 24 and a cover body 26. A side edge of the cover body 26 is pivotally connected to a side edge of the base body 24. The cover body 26 can be opened and closed relative to the base body 24. The base body 24 includes a first inner shell 241 and a first outer shell 242. A first guiding space 243 is formed between the first inner shell 241 and the first outer shell 242. The cover body 26 includes a second inner shell 261 and a second outer shell 262. A second guiding space 263 is formed between the second inner shell 261 and the second outer shell 262. When the cover body 26 and the base body 24 are closed, a second accommodation space 27 is surrounded and defined by the first inner shell 241 and the second inner shell 261. The first guiding space 243 and the second guiding space 263 are interconnected for insertion of the lower shell 18 and the upper shell 20, which are closed, of the first connector bracket 12 for axial docking. The second accommodation space 27 has a third opening end 271 and a fourth opening end 272 (marked in FIG. 3 described below) opposite to each other. In one embodiment, the first inner shell 241, the second inner shell 261, the first outer shell 242 and the second outer shell 262 are arc-shaped shells. The first inner shell 241 and the second inner shell 261, after being closed, constitute an inner ring shell 291. The first outer shell 242 and the second outer shell 262, after being closed, constitute an outer ring shell 292. In an embodiment, the inner ring shell 291 and the outer ring shell 292 have the same central axis, and an inner diameter of the inner ring shell 291 is smaller than an inner diameter of the outer ring shell 292.

Figure 3:
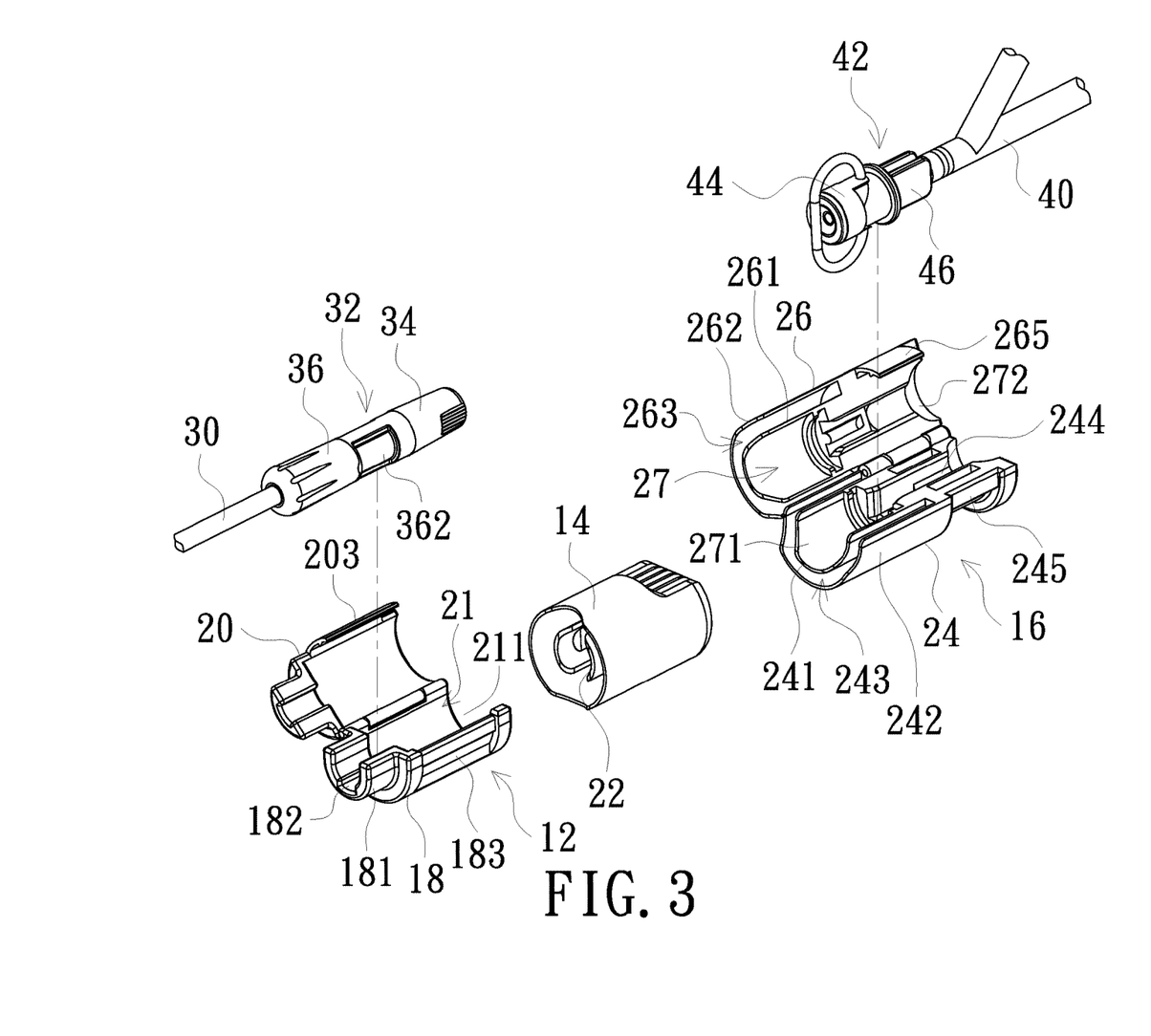
FIG. 3 is a schematic view showing an opening state of the first connector bracket and the second connector bracket of the tube-docking holding device and partial structures of a catheter and a dialysate tube according to an embodiment of the present invention.

FIG. 3 is a schematic view showing an opening state of the first connector bracket and the second connector bracket of the tube-docking holding device and partial structures of a catheter and a dialysate tube according to an embodiment of the present invention. As shown in FIG. 3, an inner side surface of a fixing portion 181 of the first connector bracket 12 is provided with a foolproof groove 182. A side edge of an outer surface of the lower shell 18 is provided with a first slot 183. A side edge of the upper shell 20 is extendedly provided with a first fastening portion 203. When the lower shell 18 and the upper shell 20 are closed, the first fastening portion 203 is fastened to the first slot 183, so as to maintain the closure of the lower shell 18 and the upper shell 20. Please continue referring to FIG. 3. In the second connector bracket 16, the first guiding space 243 and the second guiding space 263 are adjacent to the third opening end 271. The places adjacent to the fourth opening end 272, between the first inner shell 241 and the first outer shell 242 and between the second inner shell 261 and the second outer shell 262, are solid without forming the first guiding space 243 and the second guiding space 263. An inner surface of the first inner shell 241 of the base body 24 is provided with a fixing groove 244. A side edge of an outer surface of the first outer shell 242 of the base body 24 is provided with a second slot 245. A side edge of the second outer shell 262 of the cover body 26 is extendedly provided with a second fastening portion 265. When the base body 24 and the cover body 26 are closed, the second fastening portion 265 is fastened to the second slot 245, so as to maintain the closure of the base body 24 and the cover body 26. In other embodiments, the way to maintain the closure of the lower shell 18 and the upper shell 20 or to maintain the closure of the base body 24 and the cover body 26 is not limited to the use of the above-mentioned fastening methods, and gluing methods and the like may also be used.

FIG. 3 further discloses partial structures of a general catheter 30 and a general dialysate tube 40. One end of the general catheter 30 is placed into the patient's body, and the other end is connectedly provided with a first connector assembly 32. As shown in FIG. 3, the first connector assembly 32 has a first connector body 36 and a cap 34. One end of the first connector body 36 is connected to the catheter 30, and the other end has a first end portion 361 (shown in FIG. 11 described below). An outer surface of the first connector body 36 adjacent to the first end portion 361 forms a screw thread 363 (shown in FIG. 11 described below). The cap 34 can be screwed to the screw thread 363 of the first connector body 36 to cover the first end portion 361. The first end portion 361 needs to be in a sterile state. Therefore, an interior of the cap 34 is generally provided with a sterilization sleeve (not shown in the figure), so that when the cap 34 is screwed to the first connector body 36, the first end portion 361 and the screw thread 363 can be sterilized at the same time. The cap 34 is a single-use component. One end of the dialysate tube 40 is generally connected to a double-bag system (not shown in the figure), and the other end is connectedly provided with a second connector assembly 42. The second connector assembly 42 has a second connector body 46 and a pull-ring cap bushing 44. One end of the second connector body 46 is connected to the dialysate tube 40, and the other end has a second end portion 461 (shown in FIG. 11 described below). The second connector assembly 42 is a single-use component, and before use, the pull-ring cap bushing 44 is utilized to cover the second end portion 461.

Figure 4:
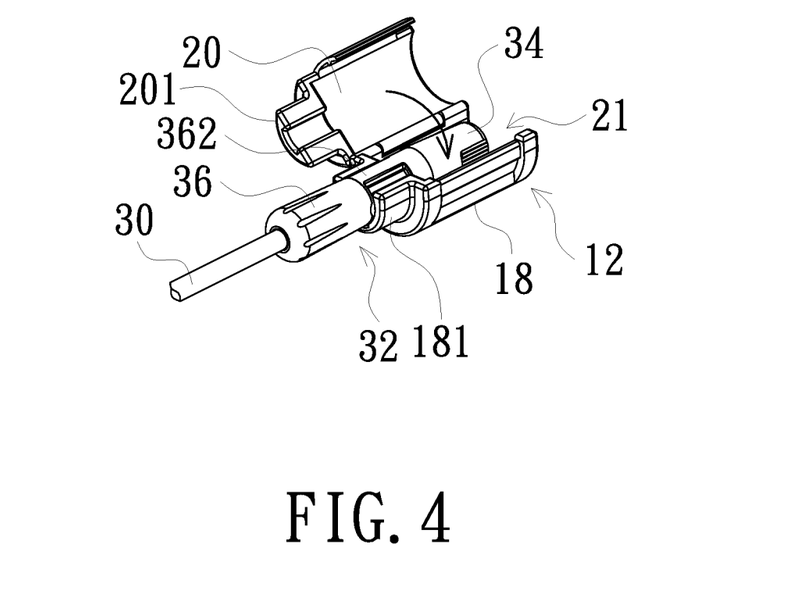
FIG. 4 is a schematic view showing an assembly process of the first connector bracket of the tube-docking holding device and the first connector assembly of the catheter according to an embodiment of the present invention.
Figure 5:
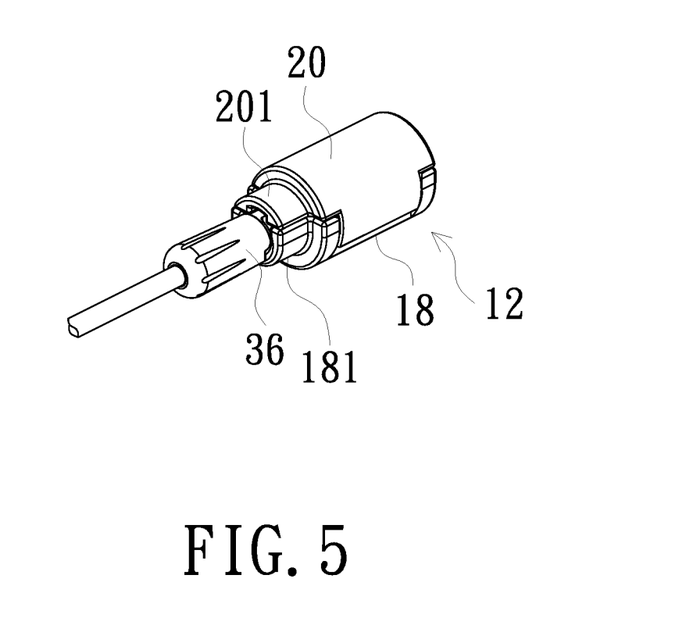
FIG. 5 is a schematic view showing the completion of assembly of the first connector bracket of the tube-docking holding device and the first connector assembly of the catheter according to an embodiment of the present invention.

FIG. 4 is a schematic view showing an assembly process of the first connector bracket of the tube-docking holding device and the first connector assembly of the catheter according to an embodiment of the present invention. FIG. 5 is a schematic view showing the completion of assembly of the first connector bracket of the tube-docking holding device and the first connector assembly of the catheter according to an embodiment of the present invention. As shown in FIG. 4, when the first connector bracket 12 is assembled with the first connector assembly 32 of the catheter 30, the upper shell 20 is open relative to the lower shell 18, and a portion of the first connector body 36 of the first connector assembly 32 is placed at the arc-shaped fixing portion 181. In an embodiment, a portion of an outer surface of the first connector body 36 is provided with a foolproof bulge 362. The foolproof bulge 362 is fastened to the foolproof groove 182 (shown in FIG. 3) of the fixing portion 181. After a portion of the first connector body 36 together with the cap 34 is located in the first accommodation space 21, referring also to FIG. 5, the upper shell 20 is closed relative to the lower shell 18, and the clamping space 213 (shown in FIG. 1) formed by the two fixing portions 181 and 201 tightly clamps the first connector body 36.

Figure 6:
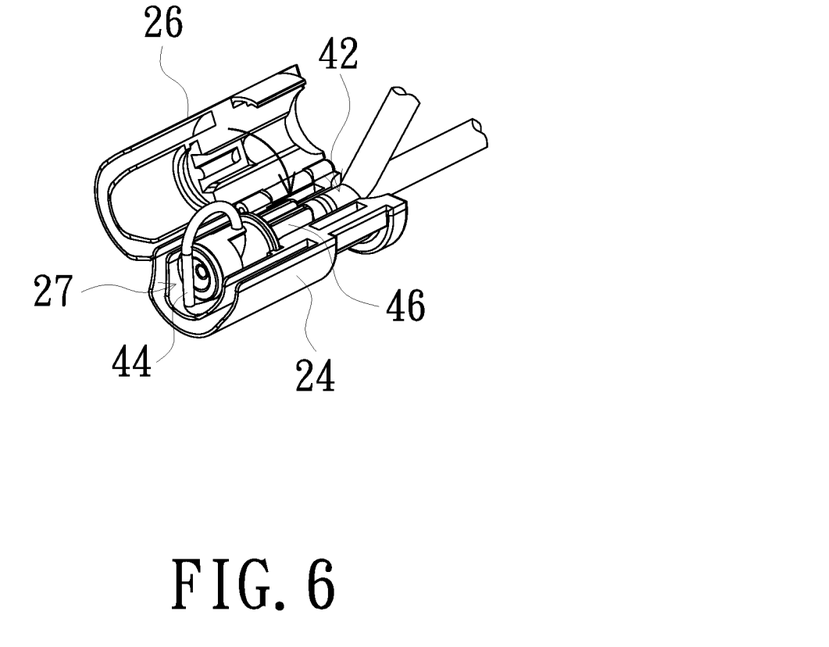
FIG. 6 is a schematic view showing an assembly process of the second connector bracket of the tube-docking holding device and the second connector assembly of the dialysate tube according to an embodiment of the present invention.
Figure 7:
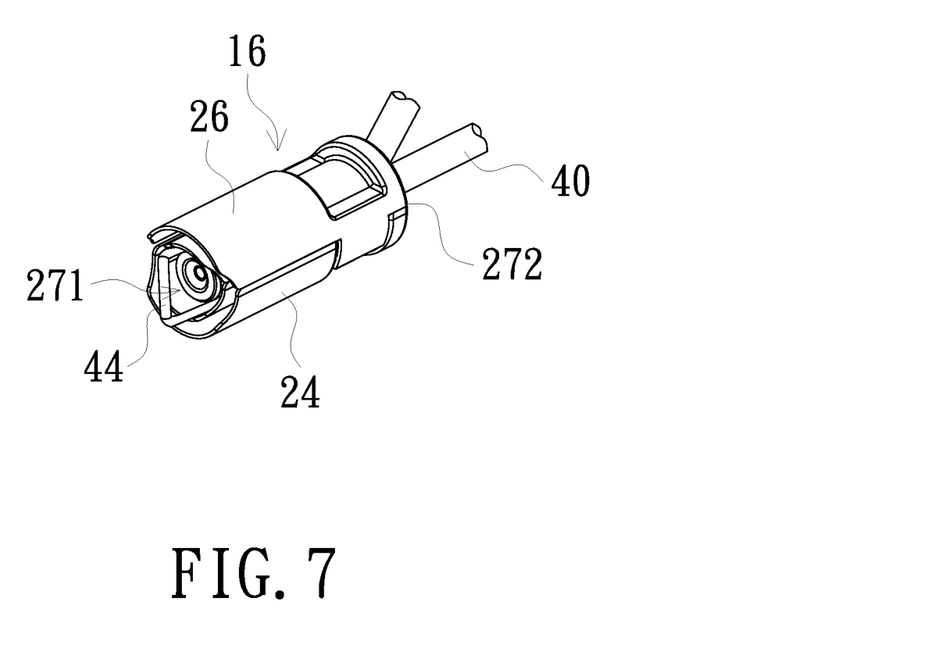
FIG. 7 is a schematic view showing the completion of assembly of the second connector bracket of the tube-docking holding device and the second connector assembly of the dialysate tube according to an embodiment of the present invention.

FIG. 6 is a schematic view showing an assembly process of the second connector bracket of the tube-docking holding device and the second connector assembly of the dialysate tube according to an embodiment of the present invention. FIG. 7 is a schematic view showing the completion of assembly of the second connector bracket of the tube-docking holding device and the second connector assembly of the dialysate tube according to an embodiment of the present invention. As shown in FIG. 6, the second connector body 46 is disposed in the fixing groove 244 (shown in FIG. 3) of the base body 24, so that the second connector body 46 together with the pull-ring cap bushing 44 is located in the second accommodation space 27. Next, please also refer to FIG. 7. The cover body 26 is closed relative to the base body 24, and a portion of the pull-ring cap bushing 44 is exposed outside the third opening end 271 of the second connector bracket 16, and the dialysate tube 40 is exposed outside the fourth opening end 272 of the second connector bracket 16.

Figure 8:
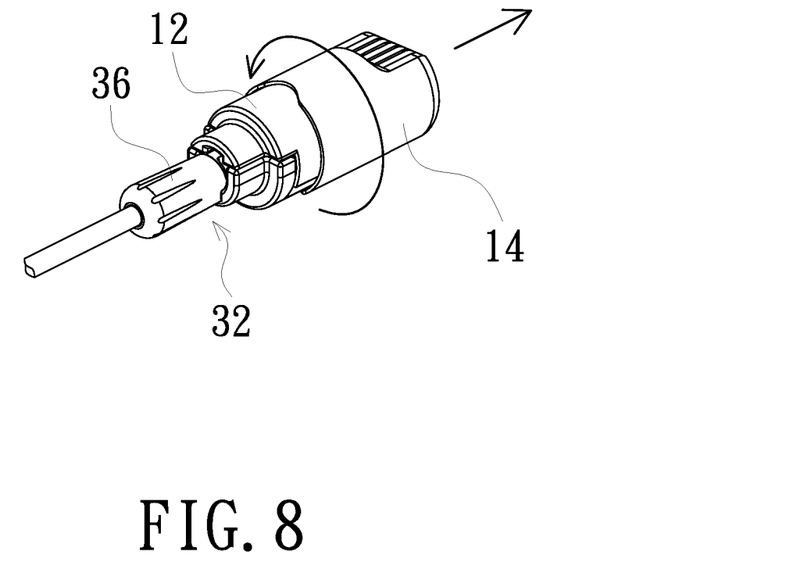
FIG. 8 is a schematic view of a cap bushing sleeved on a first connector bracket assembled with a catheter in the tube-docking holding device according to an embodiment of the present invention.
Figure 9:
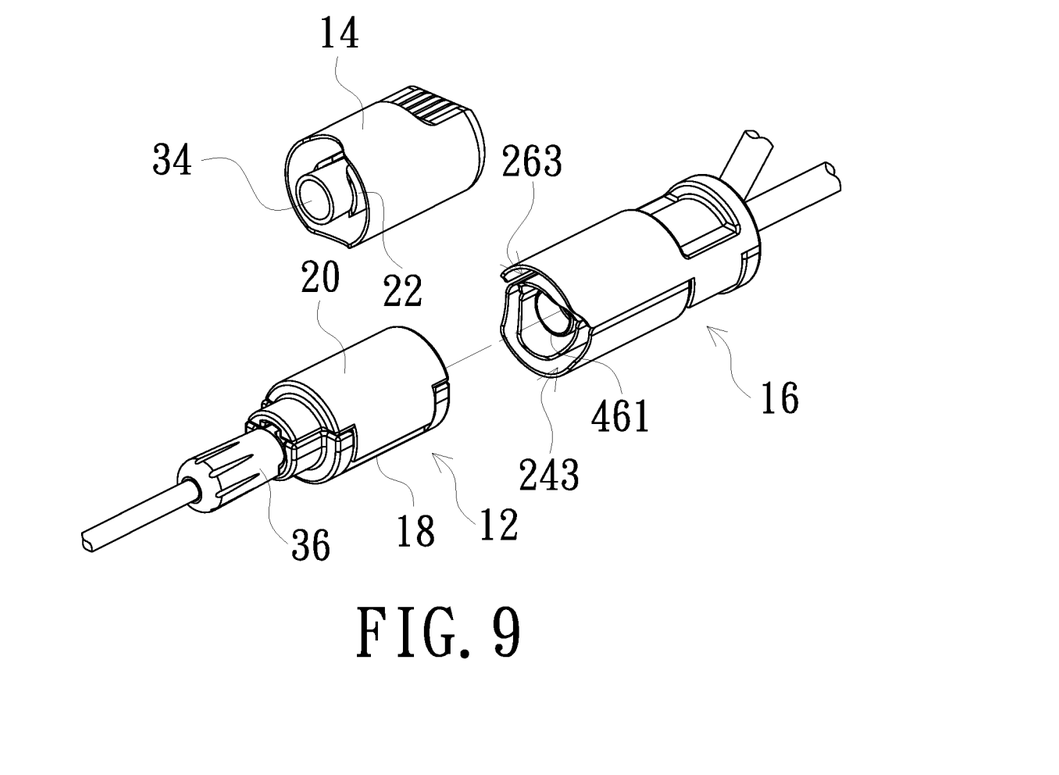
FIG. 9 is a schematic view of the tube-docking holding device before docking according to an embodiment of the present invention.

When the first connector assembly 32 completes assembly with the first connector bracket 12, as shown in FIG. 8, the cap bushing 14 is sleeved on the first connector bracket 12, so that the two clamped holding portions 22 (shown in FIG. 1) of the cap bushing 14 are placed into the first accommodation space 21 (shown in FIG. 3) to clampedly hold the cap 34 (shown in FIG. 4). By rotating the cap bushing 14 to drive the cap 34 to rotate, for example, counterclockwise, the cap 34 is disengaged from the first connector body 36 to which the cap 34 was originally screwed. When the cap bushing 14 is separated from the first connector bracket 12, the cap 34 is simultaneously clamped away from the first connector body 36 by the two clamped holding portions 22. As shown in FIG. 9, before or after the cap 34 is separated from the first connector body 36 to expose the first end portion 361 (shown in FIG. 11 described below), the pull-ring cap bushing 44 (shown in FIG. 6) of the second connector assembly 42 (shown in FIG. 6) assembled in the second connector bracket 16 is also removed by fingers (not shown in the figure) to expose the second end portion 461.

Figure 10:
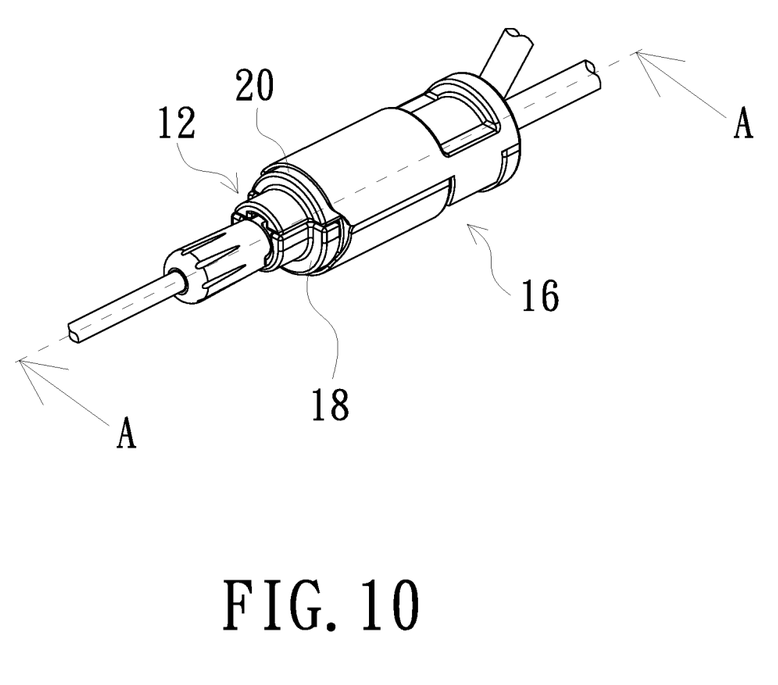
FIG. 10 is a schematic view showing the completion of docking of a tube-docking holding device according to an embodiment of the present invention.
Figure 11:
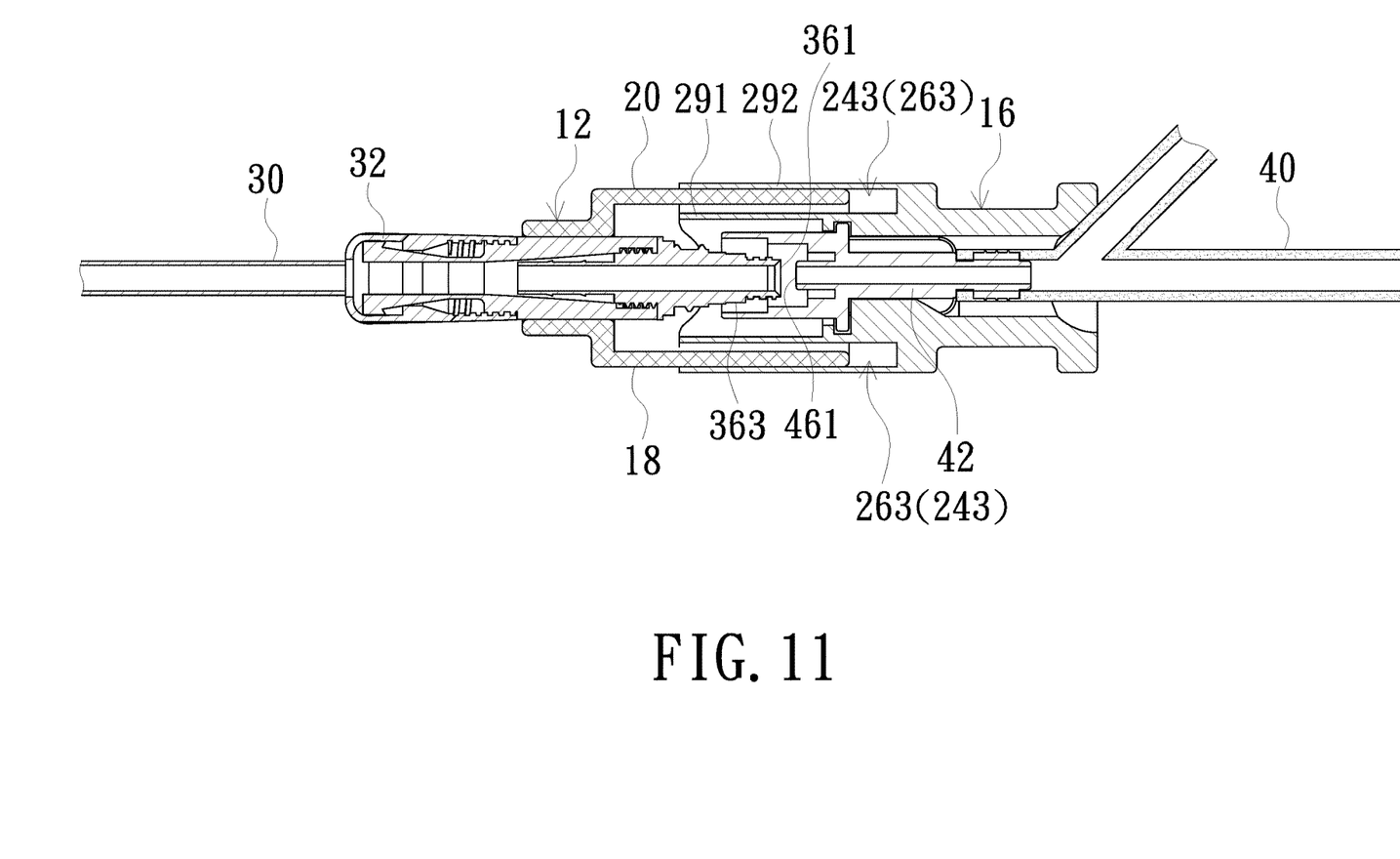
FIG. 11 is a schematic cross-sectional view taken along line A-A of FIG. 10.

FIG. 10 is a schematic view showing the completion of docking of a tube-docking holding device according to an embodiment of the present invention. FIG. 11 is a schematic cross-sectional view taken along line A-A of FIG. 10. As shown in FIG. 9 and FIG. 10, the lower shell 18 and the upper shell 20 of the first connector bracket 12 are inserted into the first guiding space 243 and the second guiding space 263 of the second connector bracket 16, so that the first connector bracket 12 and the second connector bracket 16 are axially docked. In one embodiment, the first connector bracket 12 can be rotated, for example, clockwise, so that the first connector bracket 12 is firmly screwed and docked to the second connector bracket 16. When docking is completed, as shown in FIG. 11, the first end portion 361 corresponds to the second end portion 461 to start a dialysate replacement process.

When the lower shell 18 and the upper shell 20 of the first connector bracket 12 are inserted into the first guiding space 243 and the second guiding space 263 which are interconnected, the lower shell 18 and the upper shell 20 only touch the outer ring shell 292 without touching the inner ring shell 291. Therefore, dust that may be generated by sliding or rotation for insertion due to mutual friction between the lower shell 18/the upper shell 20 and the outer ring shell 292 will only fall within the first guiding space 243 and the second guiding space 263 without contaminating the first end portion 361 and the second end portion 461 which are sterile.

After the dialysate replacement process is completed, the first connector bracket 12 is rotated, for example, counter-clockwise, so as to separate the first connector bracket 12 from the second connector bracket 16. In a figure not shown, the cap bushing 14 is utilized to clampedly hold a new cap 34 and again the cap bushing 14 is sleeved on the first connector bracket 12. By rotating the cap bushing 14 to drive the cap 34 to rotate, for example, clockwise, the new cap 34 is screwed tight to the first connector body 36 to ensure that the liquid from the catheter 30 does not overflow.

In the above embodiments, the second connector bracket has a guiding space formed by the first inner shell/the second inner shell and the first outer shell/the second outer shell, and the first connector bracket is a single-layer shell. Therefore, when docking and insertion are conducted, the first connector bracket is inserted into the guiding space of the second connector bracket, but is not limited thereto. In another embodiment, the first connector bracket may also have a guiding space formed by the inner shells and the outer shells, and the second connector bracket is a single-layer shell. Therefore, when docking and insertion are conducted, the second connector bracket is inserted into the guiding space of the first connector bracket.

In summary, the present invention can achieve the following effects:

(1) Using the tube-docking holding device according to an embodiment of the present invention, the first connector assembly of the catheter and the second connector assembly of the dialysate tube can be directly installed without changing the existing structures.

(2) Using the tube-docking holding device to clamp the first connector assembly and the second connector assembly, and then performing axial docking, can provide assistance on use to patients with physical limitations such as vision loss or hand tremors. For example, the docking can be completed with the eyes closed or without having to see clearly. Or patients can be prevented from touching the sterile end portions of the connector assemblies due to hand tremors.

(3) The tube-docking holding device can be cleaned and reused or discarded. The tube-docking holding device covers the sterile end portions of the connector assemblies to provide physical isolation to prevent the end portions from contacting with dust or other contaminants, thereby helping reduce the possibility of contamination when the catheter and the dialysate tube are connected or disconnected.

(4) In the tube-docking holding device, whether the first connector bracket has a double-shell structure with a guiding space formed by the inner shells and the outer shells, or the second connector bracket does, the chance of falling dust to the end portions, after the first connector bracket and the second connector bracket are docked and rubbed, can be avoided. Therefore, after the first connector bracket and the second connector bracket are combined, the chance of contamination of the end portions of the connector bodies can be greatly reduced.

(5) The cap bushing can be used to assist in unscrewing the cap from the first connector body or re-screwing the new cap to the first connector body. Therefore, under the premise of not touching the sterile end portion of the first connector body of the catheter, docking and disconnection with the dialysate tube can be completed.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A tube-docking holding device, adapted for docking a catheter with a dialysate tube for peritoneal dialysis, wherein one end of the catheter is placed into a patient's body, the other end of the catheter is located outside the patient's body and is connectedly provided with a first connector assembly, one end of the dialysate tube is connected to a double-bag system, the other end of the dialysate tube is connectedly provided with a second connector assembly, and the tube-docking holding device comprises:

a first connector bracket, comprising a lower shell and an upper shell, wherein the upper shell is configured to be opened and closed relative to the lower shell, and when the upper shell and the lower shell are closed, a first accommodation space is surrounded and defined for fixing a portion of the first connector assembly, wherein the first accommodation space has a first opening end and a second opening end opposite to each other, the lower shell and the upper shell are respectively provided with a fixing portion at an end adjacent to the second opening end; and a second connector bracket, comprising a base body and a cover body, wherein the cover body is configured to be opened and closed relative to the base body, the base body comprises a first inner shell and a first outer shell, a first guiding space is formed between the first inner shell and the first outer shell, the cover body comprises a second inner shell and a second outer shell, a second guiding space is formed between the second inner shell and the second outer shell, when the cover body and the base body are closed, the first inner shell and the second inner shell surround and define a second accommodation space for fixing a portion of the second connector assembly, and the first guiding space and the second guiding space are interconnected for insertion and docking of the lower shell and the upper shell which are closed, wherein the second accommodation space has a third opening end and a fourth opening end opposite to each other, an inner surface of at least one of the first inner shell and the second inner shell is provided with a fixing groove, wherein the first connector assembly comprises a first connector body having a first end portion, the second connector assembly comprises a second connector body having a second end portion, a portion of the first connector body is configured to place at the one of the fixing portion when the upper shell is open relative to the lower shell, and then the portion of the first connector body is clamped by the two fixing portions when the upper shell is closed relative to the lower shell, so that a portion of the first connector body and the first end portion are located in the first accommodation space, the first end portion is toward the first opening end, and the catheter is exposed outside the second opening end, and a portion of the second connector body is configured to place at the fixing groove when the cover body is open relative to the base body, and then the second end portion is located in the second accommodation space when the cover body is closed relative to the base body, wherein the second end portion is toward the third opening end, and the dialysate tube is exposed outside the fourth opening end.

2. The tube-docking holding device according to claim 1, further comprising a cap bushing, an interior of which is provided with two clamped holding portions, wherein the cap bushing is sleeved on the first connector bracket to cover the first opening end, the first connector assembly further comprises a cap, the cap is screwed to the first connector body and covers the first end portion, the two clamped holding portions of the cap bushing can be used for being placed into the first accommodation space and clampedly holding the cap, and the cap and the first connector body are configured to be separated through actuation of the cap bushing.

3. The tube-docking holding device according to claim 1, further comprising a cap bushing, an interior of which is provided with two clamped holding portions configured to clamp a cap, wherein the cap bushing is configured to be sleeved on the first connector bracket to cover the first opening end, the two clamped holding portions clamping the cap are placed into the first accommodation space, and the cap clamped by the two clamped holding portions is screwed to the first connector body through actuation of the cap bushing.

4. The tube-docking holding device according to claim 1, wherein an inner side surface of at least one of the fixing portions forms a foolproof groove.

5. The tube-docking holding device according to claim 1, wherein the lower shell and the upper shell are arc-shaped shells, and the lower shell and the upper shell, after being closed, form a hollow cylindrical shape.

6. The tube-docking holding device according to claim 1, wherein a side of the upper shell is pivotally connected to the lower shell, a side edge of an outer surface of the lower shell is provided with a first slot, a side edge of the upper shell is extendedly provided with a first fastening portion, and when the lower shell and the upper shell are closed, the first fastening portion is fastened to the first slot.

7. The tube-docking holding device according to claim 1, wherein the first inner shell, the second inner shell, the first outer shell and the second outer shell are arc-shaped shells, the first inner shell and the second inner shell, after being closed, constitute an inner ring shell, the first outer shell and the second outer shell, after being closed, constitute an outer ring shell, the inner ring shell and the outer ring shell have the same central axis, and a diameter of the inner ring shell is smaller than a diameter of the outer ring shell.

8. The tube-docking holding device according to claim 1, wherein a side of the cover body is pivotally connected to the base body, a side edge of an outer surface of the base body is provided with a second slot, a side edge of the cover body is extendedly provided with a second fastening portion, and when the base body and the cover body are closed, the second fastening portion is fastened to the second slot.

\* \* \* \* \*